(12) United States Patent
Paul, Jr.

(10) Patent No.: US 7,887,847 B2
(45) Date of Patent: Feb. 15, 2011

(54) NUTRITIONAL SUPPLEMENT FOR TREATMENT OF OCULAR DISEASES

(76) Inventor: Edward L. Paul, Jr., Atlantic Medical Research and Development, P.O. Box 1443, Wrightsville Beach, NC (US) 28480

( * ) Notice: Subject to any disclaimer, the term of this patent is extended or adjusted under 35 U.S.C. 154(b) by 1057 days.

(21) Appl. No.: 11/122,481

(22) Filed: May 5, 2005

(65) Prior Publication Data

US 2005/0249821 A1     Nov. 10, 2005

Related U.S. Application Data

(60) Provisional application No. 60/569,364, filed on May 8, 2004.

(51) Int. Cl.
*A61K 33/34* (2006.01)
*A61K 9/00* (2006.01)

(52) U.S. Cl. ........................ 424/638; 424/400

(58) Field of Classification Search .................. 424/400, 424/638
See application file for complete search history.

(56) References Cited

U.S. PATENT DOCUMENTS

| | | | |
|---|---|---|---|
| 5,075,116 A | 12/1991 | LaHaye et al. | 424/617 |
| 5,310,764 A | 5/1994 | Baranowitz et al. | 514/725 |
| 5,976,568 A | 11/1999 | Riley | 424/451 |
| 6,579,544 B1 | 6/2003 | Rosenberg et al. | 424/746 |
| 6,649,195 B1 * | 11/2003 | Gorsek | 424/732 |
| 6,660,293 B2 | 12/2003 | Giordano et al. | 424/439 |
| 6,660,297 B2 | 12/2003 | Bartels et al. | 424/464 |

OTHER PUBLICATIONS

Rowe et al, Handbook of Pharmaceutical Excipients, 2003, Pharmaceutical Press, Fourth Edition, p. 27-29.*

* cited by examiner

*Primary Examiner*—Fereydoun G Sajjadi
*Assistant Examiner*—Gigi Huang
(74) *Attorney, Agent, or Firm*—Michael E. Mauney

(57) ABSTRACT

A nutritional supplement composition that promotes visual health and reduces or reverses visual acuity loss by a reduced Vitamin E content from standard supplements with the addition of taurine, omega-3 fatty acids, and non proform Vitamin A carotenoids including lutein and zeaxanthin. The essential ingredients of the nutritional or dietary supplements are Vitamin C, no more than 300 IUs of Vitamin E, Vitamin A at least a portion of which is provided in the form of a proform Vitamin A carotenoid, omega-3 fatty acids, and non proform Vitamin A carotenoids including lutein and/or zeaxanthin. The essential ingredients are provided in a form suitable of oral ingestion or other forms of administration in one or more doses per day.

10 Claims, No Drawings

NUTRITIONAL SUPPLEMENT FOR TREATMENT OF OCULAR DISEASES

RELATED APPLICATION

This application claims the benefit of U.S. Provisional Application Ser. No. 60/569,364, accorded a filing date of May 8, 2004.

FIELD OF THE INVENTION

The present invention relates to a nutritional supplement composition that helps prevent, stabilize, or reverse, the loss of visual acuity resulting from particular ocular diseases. More specifically it relates to a nutritional supplement for treatment of retinal diseases including age related macular degeneration, retinitis pigmentosa, Stargardt's disease, diabetic retinopathy, macular dystrophies, and cataracts.

BACKGROUND OF THE INVENTION

The macula is the area of the retina which in humans is responsible for central vision. It is centered around the area where the visual axis meets the retina and extends radially outward a distance about 2.75 mm or one-tenth of one inch. The macula is divided into an inner and outer macula. The outer macula is an annular ring surrounding the inner macula. Although small, the macula has the highest degree of visual acuity. Diseases that disrupt the functioning of the macula substantially affect the vision of a patient with one of those diseases. Once such disease is age related macular degeneration (AMD). It has been found that this occurs in approximately 20 percent of the population above the age of 65 and it is a leading cause of visual impairment in industrialized countries. A portion of the macula has a layer of pigmented epithelial known as the retinal pigment epithelium (RPE). It is believed that macular degeneration is caused by disruption, deterioration, or death of the retinal pigment epithelium cells. AMD is usually diagnosed by collection of clinical findings. These include drusen, retinal pigmented epithelial disturbance, which includes pigment clumping, RPE detachment, geographic atrophy, sub-retinal neovascularization, or disciform scar. The presence of drusen alone do not seem to be directly associated with vision loss and, indeed, up to 85 percent of people are found to have drusen upon ocular examination.

Although the exact cause of macular degeneration is unknown, it is believed the onset and progression of macular degeneration is accelerated by toxicity from free radicals and oxidizers. It is believed that oxidants including singlet oxygen and other free radicals can occur as result of phototoxicity. That is to say, the presence of light can react with the presence of oxygen to produce singlet oxygen, a free radical, leading to potential damage from chemical reactions between the physiological structures that constitute the macula and these oxidizing agents including singlet oxygen.

It is known that naturally occurring substances that humans intake with a normal diet can serve as antioxidants and free radical scavengers, possibly reducing or eliminating tissue damage from oxidation or the presence of free radicals in those tissues. More specifically, it has been reported that high-dose supplementation with Vitamin C and E, beta-carotene, and zinc had a clinically significant affect on the occurrence and progression of macular degeneration and vision loss (see Age-Related Eye Disease Study Research Group: "A Randomized Placebo-Controlled Clinical Trial of High-Dose Supplementation of Vitamin C and E, Beta-carotene and Zinc for Age Related Macular Degeneration and Vision Loss: AREDS Regular Report No. 8 ", *Archives of Ophthalmology*, Volume 119, No. 10 Oct. 2001, pages 1417-1436). In the AREDS study, a nutritional substance was evaluated. This substance contained 500 mgs of Vitamin C, 400 IUs of Vitamin E, 15 mgs of beta-carotene, 80 mgs of Zinc, and 2 mgs of copper. Vitamins C, E, and beta carotene are known antioxidants. Vitamin C and beta-carotene are water soluble. On the other hand, Vitamin E is a fat soluble vitamin. For water soluble vitamins, the excess is excreted from the body, but fat soluble vitamins are stored and can accumulate in the liver, fat, and muscle tissues. There have been some negative reactions associated with mega doses of Vitamin E, which includes headache, fatigue, diplopia, and diarrhea. Animal studies have shown that high doses of Vitamin E may interfere with absorption of other fat soluble vitamins. Consequently, there is a concern that large doses of Vitamin E consumed over weeks or months may result in deficiencies of Vitamins D, A, and K.

Vitamin A has been shown to slow the progression of retinitis pigmentosa (RP). However, Vitamin E has shown to be potentially harmful. Vitamin E may interfere with the absorption of Vitamin A, hence, can reduce the effectiveness of Vitamin A intake in slowing the progression of RP.

Vitamin C is a well-known water soluble antioxidant. Humans must consume sources of Vitamin C to meet the Vitamin C requirements for normal physiological functioning. The recommended daily allowance (RDA) for Vitamin C in the form of ascorbic acid is 60 mgs. However, large daily doses of Vitamin C have been taken over many years with no undesirable effects. Intakes of 1000 mgs or more have been consumed daily without adverse affects.

Beta-carotene is a proform of Vitamin A. Beta-carotene is a water soluble orange pigment found in many vegetables. In the body beta-carotene is converted to Vitamin A with efficiency approximately 50 percent. The RDA of Vitamin A is 5000 IUs. It is understood that beta-carotene is a highly effective antioxidant. There have been adverse effects associated with high doses of beta carotene for people with myocardial infarctions. There is also a reported increase of lung cancer among smokers who receive upwards of 20 mgs a day of beta-carotene. Beta-carotene is a carotenoid. Another naturally occurring carotenoid is lutein. Lutein is the primary carotenoid present in the macula. It is believed that lutein may act as a filter to protect the macula from potentially damaging forms of light. There is evidence to suggest that people who eat more lutein containing foods appear to be at a lower risk of macular degeneration than the population at large. One study has found that adults with the highest dietary intake of lutein had a 57 percent decreased risk of macular degeneration compared with people with the lowest intake. For this reason, lutein may be used in a dietary supplement to supplement or substitute for beta-carotene. Another naturally occurring carotenoid is zeaxanthin. Like lutein and beta-carotene, zeaxanthin is an antioxidant found in the retina of healthy eyes. It is believed that the presence of these carotenoids in the retina of healthy eyes tends to protect against damage from phytotoxicity, free radicals, and other oxidizing agents. Consequently, it has been found that dietary supplements containing an appropriate combination of the carotenoids, beta-carotene, lutein, and/or zeaxanthin may be necessary for healthy eyes.

In addition to the carotenoids, a variety of other compounds have been found to have antioxidant qualities. For example, alpha-lipoic acid may enhance the potency of other antioxidants in the body. Phenolic compounds can also serve as useful antioxidants. Some of these phenolic compounds are found naturally in grape seeds. The anthocyanosides are also useful antioxidants that are found naturally in bilberry fruit.

Zinc is one of the essential minerals that forms a part of many enzymes which are physiologically important, including those that are involved in digestion, metabolism, reproduction, and wound healing. High doses of Zinc have been associated with anemia. It is believed that the anemia associated with high Zinc intake is attributable to Copper deficiency. Consequently, it is usually thought desirable for a nutritional supplement that includes high doses of Zinc that there also be included some intake of Copper. Copper, like Zinc, is important in various bodily enzymes. Therefore, adding Copper to a nutritional supplement to accompany Zinc will reduce the risk of Zinc intake leading to a Copper deficiency. Even though it is widely understand that nutritional supplements containing antioxidants in various forms and mineral supplements may be useful in promoting retinal health and preventing age-related retinal diseases, work still remains to be done to determine exactly what balance of nutritional supplements in what proportions and what ingredients will provide the best protection.

BACKGROUND ART

Bartels et al., U.S. Pat. No. 6,660,297 discloses a nutritional supplement to treat macular degeneration. The essential ingredients disclosed in the Bartels application are Vitamin C, Vitamin E, beta-carotene, Zinc, and Copper. The Bartels patent suggests that at least 400 IUs of Vitamin E should be taken on a daily basis. However, recent studies have shown that doses of Vitamin E of 400 IUs and greater apparently lead to an increased risk of death in a study population (See Miller et al.,: *High Dosage Vitamin E Supplementation May Increase All—cause Mortality*. Ann. Intern. Med., 2004, November 10). Baranowitz, U.S. Pat. No. 5,310,764, also suggests the use of beta-carotene for treatment of age-related macular degeneration. Baranowitz suggests that beta-carotene may be supplemented to a patient using a commercially available form of beta-carotene, suggesting one such product sold by Hoffman-LaRosch under the trademark "Solatene." Synthetic beta-carotene consists of one molecule called "trans beta-carotene." However, recent research has suggested that synthetic beta-carotene may cause an increased risk of lung cancer and disease of the blood vessels. Natural beta-carotene consisting of two molecules, trans beta-carotene and 9-cis beta-carotene, has an antioxidant activity that the synthetic form of beta-carotene lacks. Other background art also suggests the desirability of using carotenoids as part of a vitamin supplement. For example, Giordano et al., U.S. Pat. No. 6,660,293, suggests the utility of carotenoids, which are typically beta-carotene, alpha-carotene, lutein, crypthoxanthine, and zeaxanthin. Gorsek, U.S. Pat. No. 6,649,195, suggests a vitamin composition including Vitamin A. The preferred formulation for Vitamin A uses natural carotenoids, beta-carotene, alpha-carotene, lutein, zeaxanthin, crypthoxanthine, and palmitate. The above patents did not distinguish between natural beta-carotene containing trans beta-carotene and 9-cis beta-carotene from synthetic beta-carotene.

Consequently, it is an object of the current invention to provide a nutritional supplement which will not only be useful for treatment of retinal diseases, including age-related macular degeneration, retinitis pigmentosa, but also be useful in relation to Stargardt's disease, diabetic retinopathy, macular dystrophies, and cataracts. The present invention preferably comprises an effective amount of specific antioxidants, amino acids, fatty acids and mineral supplements to decrease visual acuity loss from various ocular diseases. It is an object of the current invention to provide a nutritional or dietary supplement composition comprising an effective amount of specific antioxidants, Zinc, and other ingredients that will treat a variety of diseases that can decrease visual acuity. It is also an object of this invention to provide a safe dietary supplement, while avoiding any potential complications arising from high doses of fat soluble Vitamin E.

DETAILED DESCRIPTION OF THE COMPOSITION

The following detailed description is designed to provide a person of skill in the art to make and use this invention and it sets forth the best composition contemplated by the inventor to achieve the objects of the invention as set out above.

Antioxidants

Vitamin C—It is well understood that Vitamin C is a water soluble antioxidant. Vitamin C in the form of ascorbate is found in the aqueous humor of the human eyes. It is believed that maximum aqueous humor ascorbate concentration occurs at the blood plasma ascorbate level in a range of 0.3 to 0.5 mgs per deciliter (mg/dl). The recommended dietary allowance for Vitamin C in the form of ascorbic acid is 60 mgs. Historical data suggests that very large daily doses of Vitamin C taken over many years have no undesirable effects. Intakes a 1000 mgs or more of Vitamin C have been taken daily without any adverse effects. Consequently, it is believed that effectively a formulation should provide a dosage of 452 mgs of Vitamin C for the provided in one daily tablet or split into dosages of two or more tablets to be taken daily. The total daily intake of Vitamin C should amount to 452 mgs. The tablets themselves may contain somewhat more than is necessary to amount to 452 mgs of a daily total dosage. The excess Vitamin C in the form of ascorbic acid may be used to compensate for natural degradation of the ascorbic acid over the shelf life of the tablet. Consequently, it is proposed that the effective daily dosage for Vitamin C is no more than 500 mgs. As an antioxidant, Vitamin C provides many helpful benefits to a user. It may protect LDL cholesterol from oxidative damage. It also may reduce stiffness of arteries and the tendency of platelets to clump together. It may protect smokers and individuals exposed to secondary smoke from the harmful effects of free radicals created by tobacco smoke. Vitamin C may improve nitric oxide activity which is needed for dilatation of blood vessels. Studies have shown Vitamin C improves the function of cells lining blood vessels. Consequently, Vitamin C is believed to be effective in slowing the progression of age-related macular degeneration. It may do so both by acting as an antioxidant directly on free radicals or other oxidants which can damage the macula cells, but also may improve the function of the blood supply to the cells constituting the macula, hence, may act in that way to slow or reverse the progression of age-related macular degeneration. Vitamin C has been reported to reduce the enzyme Aldose Reductase. Aldose Reductase is the enzyme responsible for accumulation of sorbitol in eyes, nerves, and kidneys of people with the disease of diabetes. Accumulation of sorbitol is believed to be responsible for deterioration of the eyes, nerves, and kidneys of diabetics.

Vitamin E—Vitamin E is a known antioxidant that acts to protect cell membranes and other fat soluble parts of the body from damage from oxidants and free radicals. This includes the low density lipoprotein (LDL) cholesterol. Vitamin E plays a role in the body's ability to process glucose. Some trial suggest that Vitamin E supplementation may prove helpful in the prevention of treatment of diabetes. Vitamin E is also known to act on inflammation, blood cell regulation, connective tissue growth, and genetic control of cell division. The RDU for Vitamin E is 15 mgs or approximately 22 IUs per day. Some studies have suggested 400 to 800 IUs per day may be useful in reversing or slowing the progression of age-related macular degeneration. However, leading researchers suggest taking only 100 to 200 IUs per day of Vitamin E. Trials exploring the long term effects of different supplemental levels suggest that there is no further benefit beyond 100 to 200 IUs per day. These results, coupled with other results that suggest mega doses of Vitamin E of over 300 IUs per day may produce headaches, fatigue, diplopia, and diarrhea, suggest that dosages should be limited to less than 300 IUs per day. Animal studies have suggested that large doses of Vitamin E may interfere with the absorption of other fat soluble vitamins including Vitamins D, A, and K. Consequently, it is believed that the appropriate dosage level for Vitamin E should not exceed 300 IUs with the preferable dosage in the range of 200 IUs. The preferred daily dosage of 200 IUs may be provided in one pill or may be split into two or more pills to be taken daily. There may be natural degradation of the Vitamin E in the pills within the shelf life of the nutritional supplement. Consequently, as much as 30 percent additional Vitamin E may be added to compensate for the natural degradation of the shelf life, but in no event should the daily dosage of Vitamin E exceed 300 IUs.

Vitamin A—Vitamin A may be provided in the form of Vitamin A and as beta-carotene, a proform of Vitamin A. Vitamin A is a fat soluble vitamin with major functions in the body. It aids in cell reproduction, hence, aiding the maintaining of healthy cells in various structures of the eye. Vitamin A is also required by the cells in the eye for transduction of light into nerve signals in the retina. For some people, water soluble forms of Vitamin A (beta-carotene) appear to be better absorbed than fat soluble Vitamin A. Beta-carotene is a member of the carotenoid family, which includes cryptosantin, alpha-carotene, zeaxanthin, lutein, and lycopene. However, unlike beta carotene, these members of the carotenoid family are not converted to Vitamin A in significant amounts. It is believed that a combination of Vitamin A and beta-carotene provides the best overall Vitamin A nutritional supplement. It is believed that approximately 15,000 IUs of Vitamin A and no more than 20,000 IUs as beta-carotene is the appropriate daily amount. Natural beta-carotene is required. Studies have suggested that synthetic beta-carotene has caused an increased risk of lung cancer and diseases of the blood vessels. Other studies have shown that the natural form of beta-carotene has an antioxidant activity that the synthetic form lacks. This may be split into more than one tablet to be taken daily to amount to the total amount. To protect against natural degradation of Vitamin A and beta-carotene during the shelf life of the supplements, appropriate increases in the amount in each tablet may be added in order to arrive at the preferred daily dosage of 10,000 IUs as Vitamin A and 18,640 IUs as natural beta-carotene.

Lutein—Lutein is an antioxidant of the carotenoid family. It is the primary carotenoid present in the central area of the retina called the macula. It is believed lutein may act as a filter to protect the macula against damaging forms of light. Studies have shown that people who eat more lutein containing foods appear to be a lower risk of macular degeneration. Of the carotenoids, lutein is the most strongly associated with this protection. There are other preliminary studies that low dietary Lutein may also increase the risk of cataracts. It is believed that approximately 8 mgs of lutein per day as a dietary supplement is most likely to achieve the protective effects associated with lutein for diseases that affect visual acuity. As before, this may be provided in a single dietary tablet taken once a day or may be split into two or more tablets to be taken daily. The desirable consumption is 8 mgs a day. The tablet, or tablets, may provide more than 8 mgs of Lutein to guard against degradation naturally associated over the shelf life of the tablet.

Minerals

Zinc and Copper—Zinc is an essential mineral that is a component than more than 300 enzymes. These enzymes have a wide variety of body functions, including repairing wounds, maintaining fertility in adults and growth in children, synthesize proteins, preserve vision, boost immunity, and protect against free radicals or other oxidizing agents. However, Zinc reduces the body's ability to utilize the essential mineral Copper. Consequently, in any supplement which adds significant amounts of Zinc beyond the recommended daily allowance, it is also necessary to add Copper to guard against a Copper deficiency due to the Zinc intake. Copper also is widely used in enzymes in the body. It is part of the antioxidant enzyme super oxide dismutase. Copper is also needed to make adenosine triphosphate. Consequently, it is believed in any nutritional supplement than no less than 20 mgs and no more than 80 mgs of Zinc as a daily supplement is appropriate. Again, the supplements may be split into more than one tablet as long as the total daily supplement stays within the limits as outline above. Likewise, no less than 1 mg and nor more than 2 mgs of Copper should be included in the daily supplement.

Fatty Acids

Fatty acids, specifically fatty acids obtained from fish oil, have been found to have a number of beneficial health effects. It is understood that oil from fish contains eicosapentaenoic acid (EPA) and docosahexaenoic acid (DHA). These are classified as omega-3 fatty acids. These omega-3 fatty acids derived from fish oil are known to keep blood triglycerides in check and may inhibit the progression of atherosclerosis. EPA and DHA are believed to have anti-inflammatory activity and are sometimes used as dietary supplements with inflammatory conditions, such as Crohn's disease and rheumatoid arthritis. It is believed that the omega-3 fish oil fatty acids may balance other fatty acids. When fatty acids are out of balance in the body, the body may release chemicals that promote inflammation. Omega-3 fatty acids are needed for prostaglandin. Prostaglandin are hormone-like substances that regulate dilation of blood vessels, inflammatory responses, and other critical body processes. DHA and EPA are also believed essential for nerve and eye functions. DHA comprises about 60 percent of the outer rod segments of photoreceptor cells that are used to see with by humans. Brain tissue has a substantial component of fat composed of DHA. It is believed that fish oil omega-3 fatty acids and, specifically, DHA and EPA, are useful in wet macular degeneration since these fatty acids help heal and support blood vessel walls. Studies show that eating fish several times a month may reduce the risk of developing AMD. Studies are currently underway to more scientifically test the effect of DHA supplements on macular function for Stargardt macular dystrophy and for age related macular degeneration. It is believed that these studies will confirm the value of DHA and EPA in either preventing or slowing the progression of macular degeneration. For these reasons, it is believed that not less than 100 mgs and no more than 500 mgs of EPA and not less than 100 mgs or more than 500 mgs of DHA in a nutritional supplement with any other ingredients will perform vital functions in terms protecting against loss of visual acuity due to various eye diseases including AMD. The preferred composition is 180 mgs of EPA and 120 mgs of DHA on a daily basis. This may be provided in one tablet to be taken daily or may be split into two or more doses provided in two or more tablets. The actual tablets themselves may contain slightly more than the recommended dosages in order to guard against degradation over the shelf life of the nutritional supplement.

Amino Acids

Taurine—Taurine is a sulfur containing amino acids found in various foods including egg whites, milk, fish, and meat. High concentrations of this taurine are found in heart muscle, skeletal muscle, white blood cells, and the central nervous system. In the retina there are two binding proteins specific to taurine. An intercellular concentrations are higher in the retina than any other region derived from the central nervous system. It is believed taurine plays a roll in the process of rhodopsin regeneration necessary for night vision and is used in retinal pigment epithelium and photoreceptors. Taurine is important in cell membrane physiology. It helps protect membranes from oxidant attack and helps transport nutrients across cell membranes. Diabetes increases the retina requirement for taurine. Excess glucose rapidly and specifically decreases taurine content in the retinal pigment of epithelial cells. For the above reasons, a nutritional supplement should at least provide not less than 200 mgs and not more than 600 mgs of taurine or L-taurine. Daily intake is 400 mgs. It may be taken in one daily tablet or split into two or more doses to be taken daily. The daily dose provided in the tablets may be slightly more than the preferred composition of 400 mgs to guard against degradation of the tablets over the shelf life time of the tablets.

Table One

Table one shows a composition of a daily supplement constituting the preferred embodiment of this invention.

TABLE ONE

| | |
|---|---|
| Vitamin A | 28,640 IU |
| (10,000 IU as Vitamin A, 18,640 IU as Natural Beta-Carotene) | |
| Vitamin C | 452 mg |
| Vitamin E | 200 IU |
| Zinc (as Zinc Oxide) | 69.6 mg |
| Copper (as Copper Chelate) | 1.6 mg |
| Taurine (as L-Taurine) | 400 mg |
| EPA (Eicosapentaenoic Acid) | 180 mg |
| DHA (Docosahexaenoic Acid) | 120 mg |
| Lutein | 8 mg |

The active ingredients of the above supplement may be presented in a variety of forms. The chemistry is well known to one of art. Additionally, the method of manufacturing may take a variety of forms and a number of inactive ingredients may be added to provide longer shelf life, to make the tablet more palatable or presentable, and to aid in the ease of manufacturing process. The tablets may be blended with any desired inactive ingredients, so long as the blend is uniform and the appropriate composition is reached for each tablet. The tablets may be coated or they can be placed in a caplet or capsule and contained in a carrier, such as mineral oil, to produce a soft gel.

Consequently, the above composition is preferably provided for oral administration in a variety of forms, including lacquered tablets, unlacquered tablets, caplets, or capsules. For simplicity, during the remaining portion of this description, the form of administration, whether lacquered tablets, unlacquered tablets, caplets, or capsules, will be referred to as "tablets" without distinguishing among the various forms.

The daily dosage of a subject composition, as specified above, may be administered in the form of one or more tablets. Some studies suggest that two tablets or more taken twice or more a day may increase or improve absorption and provide a better maintenance of blood levels of the ingredients as outlined in Table One. The formulation of an individual tablet is determined based on the amount of the essential ingredients that are required to be present in each tablet to total the amount of essential ingredients as outlined in Table One. The preferred form of administration is two tablets taken three times a day for a total of six tablets per day.

The actual tablets sold for consumption may contain somewhat more than the total amounts specified in Table One. The active ingredients may degrade over time. Consequently, in order to assure that the active ingredients are presented in the minimum amounts required at the time the tablets are actually ingested, may require increasing the dosage beyond the minimum amounts required in order to account for and compensate for degradation over time. Some of the essential ingredients degrade faster than others, which can result in different percentages of excess in each tablet for one essential ingredient as compared to a different essential ingredient. However, it is important that the total of the IUs of Vitamin E in the dosage remain below 300 IUs.

Although it is believed that oral ingestion through the form of a tablet is the preferred administration, there are variations in administration which could be appropriate in some circumstances. These could include time-release tablets, orally ingested liquid, intraperitoneal, intravenous, subcutaneous, sublingual, transcutaneous, intramuscular, or other forms of administration.

For each of the ingredients specified, there may be more than one source for the ingredients. For Vitamin C, ascorbic acid may be the preferred source of Vitamin C, but other forms of Vitamin C, such as sodium ascorbate, could alternatively be used in lieu of the ascorbic acid. For Vitamin E, there are a variety of forms that might be available. One form is dl-alpha tocopheryl acetate. Other forms, such as trimethyl tocopheryl acetate or Vitamin E succinate, may be used in the alternative. For Zinc, zinc oxide may be used and provides the most concentrated form of elemental Zinc. Other forms, such as zinc gluconate are alternative forms that are also acceptable. For Copper, copper oxide is a form that is frequently used in dietary supplements, but also alternative forms such as copper gluconate may be alternatively used.

EXAMPLES

Clinical trials have been conducted in compliance with the National Eye Institute Clinical Study criteria. The subjects all had age related macular degeneration. In this study there was a control group with a testing population of 43. During the study, the control group received a standard over the counter vitamin which is marketed specifically for eye health. This over the counter preparation contains 3000 IUs of beta carotene, 400 mg of Vitamin C, 200 IUs of Vitamin E, and 40 mg of Zinc. Seventy-two subjects were given a preparation made in accordance with Table 1. Testing was done at three months and at six months in accordance with the National Eye Institute Clinical Study criteria using a special eye chart referred to as the ETDRS Chart. All patients, both within the treatment and in the control group, had baseline vision worse than 20-60.

At three months, results show that in the treatment group administered a vitamin supplement made in accordance with in Table I showed 1.0 lines of improvement in visual acuity from the baseline test results. In the control group receiving the over the counter vitamin supplement there was 0.11 lines of loss in visual acuity. Consequently, the treatment group had a net gain of 1.11 lines of visual acuity over the control group. At six months, the treatment group now tested at baseline—that is to say they had lost 1 line of visual acuity from the three month testing to return to the same results they had at the time the study began. The control group, however, had lost 1.49 lines from baseline test results. At six months, the treatment group on the average had 1.49 lines better vision than did the control group.

It will be appreciated by one of skill in the art that various forms of chemical compounds may be used in lieu of the specific ones outlined in the foregoing disclosure so long as the active ingredients are delivered in any form that leads to blood absorption and appropriate blood levels of the active ingredients identified in the amounts set out in Table One. While the foregoing disclosure describes specific embodiments of the present invention, it is understood that modifications may be made without departing from the spirit and scope of the underlying invention and are not limited by the specific information or preferred embodiments disclosed above.

I claim:

1. A composition consisting of:
   (a) 60 to 500 mg of Vitamin C;
   (b) 22 to 300 IUs of Vitamin E;
   (c) 6(10,000IUs) to 9 mg (15,000 IUs) of fat soluble Vitamin A;
   (d) 11.2 (18,640 IUs) to 12 mg (20,000 IUs) of water soluble beta-carotene;
   (e) at least 8 mg of carotenoids selected from lutein, zeaxanthin and mixtures thereof;
   (f) 69.6 to 80 mg zinc;
   (g) 1 to 1.6 mg copper,
   (h) 100 to 180 mg EPA;
   (i) 100 to 500 mg DHA; and
   (j) 200 to 600 mg of taurine.

2. The composition of claim 1 wherein said Vitamin E comprises a mixture of natural Vitamin E and synthetic Vitamin E.

3. The composition of claim 1 wherein said beta-carotene includes natural beta-carotene.

4. The composition of claim 1 wherein said carotenoid is no more than 20 mg of said lutein.

5. The composition of claim 4 wherein said carotenoid is no more than 12 mg of said lutein.

6. The composition of claim 1 wherein said carotenoid comprises at least 0.25 mg of said zeaxanthin.

7. The composition of claim 1 wherein said zeaxanthin is no more than 20 mg.

8. The composition of claim 1 wherein said carotenoids are provided in the form of lutein containing trace amounts of zeaxanthin in a 20:1 weight to weight ratio of lutein to zeaxanthin.

9. The composition of claim 8 comprising no more than 20 mg of said lutein and said trace amounts of zeaxanthin.

10. The composition of claim 1 wherein said taurine comprises L-taurine.

* * * * *